(12) United States Patent
Siegel et al.

(10) Patent No.: US 9,511,230 B2
(45) Date of Patent: Dec. 6, 2016

(54) IMPLANTABLE MEDICAL LEAD FOR STIMULATION OF MULTIPLE NERVES

(71) Applicant: Nuvectra Corporation, Plano, TX (US)

(72) Inventors: Steven Siegel, North Oaks, MN (US); Michele Spinelli, Milan (IT); Scott F. Drees, Dallas, TX (US); Giancarlo Barolat, Golden, CA (US); John M. Swoyer, Blaine, MN (US)

(73) Assignee: Nuvectra Corporation, Plano, TX (US)

( * ) Notice: Subject to any disclaimer, the term of this patent is extended or adjusted under 35 U.S.C. 154(b) by 69 days.

(21) Appl. No.: 14/535,386

(22) Filed: Nov. 7, 2014

(65) Prior Publication Data

US 2015/0134041 A1    May 14, 2015

Related U.S. Application Data

(60) Provisional application No. 61/901,499, filed on Nov. 8, 2013, provisional application No. 61/923,927, filed on Jan. 6, 2014.

(51) Int. Cl.
| | |
|---|---|
| *A61N 1/05* | (2006.01) |
| *A61N 1/36* | (2006.01) |
| *A61N 1/372* | (2006.01) |

(52) U.S. Cl.
CPC ............. *A61N 1/36132* (2013.01); *A61N 1/05* (2013.01); *A61N 1/0512* (2013.01);
(Continued)

(58) Field of Classification Search
CPC .............. A61N 1/36132; A61N 1/3606; A61N 1/37247; A61N 1/37235; A61N 1/05; A61N 1/0512; A61N 1/36146; A61N 1/0588; A61N 1/36007; A61N 1/0551
See application file for complete search history.

(56) References Cited

U.S. PATENT DOCUMENTS

| | | |
|---|---|---|
| 6,941,171 B2 | 9/2005 | Mann et al. |
| 7,062,330 B1 | 6/2006 | Boveja et al. |
| (Continued) | | |

FOREIGN PATENT DOCUMENTS

| | | |
|---|---|---|
| EP | 1048317 | 11/2000 |
| WO | 03/020365 | 3/2003 |
| WO | 2008070804 | 6/2008 |

OTHER PUBLICATIONS

"EP Search", Application 14192269.0, Mar. 24, 2015.

*Primary Examiner* — Rex R Holmes
(74) *Attorney, Agent, or Firm* — Haynes and Boone, LLP; Eric Li

(57) ABSTRACT

In various examples, an apparatus includes a stimulation lead including an elongate body including a distal end and a proximal end. At least one first electrode is disposed proximate the distal end of the elongate body and is configured to stimulate a first target nerve. At least one second electrode is disposed between the at least one first electrode and the proximal end of the elongate body and is configured to stimulate a second target nerve. At least one first fixation structure is disposed between the at least one second electrode and the proximal end of the elongate body. The at least one first fixation structure is configured to anchor the stimulation lead proximate the sacrum, wherein the at least one first fixation structure is located on the elongate body and spaced a first distance proximally along the elongate body from the at least one first electrode.

20 Claims, 3 Drawing Sheets

(52) U.S. Cl.
CPC ......... *A61N 1/0551* (2013.01); *A61N 1/0558* (2013.01); *A61N 1/3606* (2013.01); *A61N 1/36007* (2013.01); *A61N 1/36146* (2013.01); *A61N 1/37235* (2013.01); *A61N 1/37247* (2013.01)

(56) References Cited

U.S. PATENT DOCUMENTS

| | | |
|---|---|---|
| 8,634,932 B1 * | 1/2014 | Ye .................. A61N 1/0558 607/116 |
| 8,706,232 B2 | 4/2014 | Su et al. |
| 8,706,233 B2 | 4/2014 | Su et al. |
| 2005/0113878 A1 | 5/2005 | Gerber |
| 2006/0020297 A1 | 1/2006 | Gerber et al. |
| 2007/0255364 A1 | 11/2007 | Gerber et al. |
| 2012/0136413 A1 | 5/2012 | Bonde et al. |
| 2013/0310706 A1 | 11/2013 | Stone et al. |

* cited by examiner

IMPLANTABLE MEDICAL LEAD FOR STIMULATION OF MULTIPLE NERVES

CROSS REFERENCE TO RELATED APPLICATIONS

This application claims the benefit of priority to U.S. Provisional Application Ser. No. 61/901,499, filed on Nov. 8, 2013, entitled "STIMULATION APPARATUSES, DEVICES, SYSTEMS, AND METHODS," and U.S. Provisional Application Ser. No. 61/923,927, filed on Jan. 6, 2014, entitled "STIMULATION APPARATUSES, DEVICES, SYSTEMS, AND METHODS," each of which is incorporated by reference herein in its entirety.

TECHNICAL FIELD

The present patent document pertains generally to a stimulation apparatus, system, and method and more particularly, but not by way of limitation, to an implantable apparatus, system, and method for stimulation of multiple nerves.

BACKGROUND

Stimulation of various nerves and tissue has been found to be a promising treatment for various conditions and/or ailments. For instance, pain, urinary urge, fecal incontinence, and epilepsy, to name a few, are indications for various nerve/tissue stimulation therapies. Various nerves and tissue are commonly targeted for stimulation therapy, including, but not limited to the sacral nerve, the pudendal nerve, the vagus nerve, the tibial nerve, and the spinal cord, to name a few.

Access to the pudendal nerve can be achieved in various ways, including a transgluteal approach, an ischiorectal fossa approach, a transobturator approach, and a transforaminal approach. The pudendal nerve arises from sacral nerve roots S2, S3, and S4. In some examples, such as, for instance, the transforaminal approach, the pudendal nerve can be accessed by following one of the sacral nerve roots S2, S3, and S4 to the pudendal nerve.

OVERVIEW

This overview is intended to provide an overview of subject matter of the present patent document. It is not intended to provide an exclusive or exhaustive explanation of the invention. The detailed description is included to provide further information about the present patent document.

The present inventors have recognized, among other things, that the subject matter can be used to stimulate one or more nerves or other tissue. The present inventors have further recognized, among other things, that the subject matter can be used with an implantable stimulation system. To better illustrate the apparatuses, systems, and methods described herein, a non-limiting list of examples is provided here:

Example 1 can include subject matter that can include a stimulation lead including an elongate body including a distal end and a proximal end. At least one first electrode is disposed proximate the distal end of the elongate body. The at least one first electrode is configured to stimulate a first target nerve. At least one second electrode is disposed between the at least one first electrode and the proximal end of the elongate body. The at least one second electrode is configured to stimulate a second target nerve. At least one first fixation structure is disposed between the at least one second electrode and the proximal end of the elongate body. The at least one first fixation structure is configured to anchor the stimulation lead proximate the sacrum, wherein the at least one first fixation structure is located on the elongate body and spaced a first distance proximally along the elongate body from the at least one first electrode.

In Example 2, the subject matter of Example 1 is optionally configured such that the at least one first electrode includes a plurality of first electrodes, and the at least one second electrode includes a plurality of second electrodes.

In Example 3, the subject matter of any one of Examples 1-2 is optionally configured such that the elongate body includes a first portion and a second portion, wherein the second portion is coaxially disposed around the first portion. The at least one first electrode is disposed on the first portion of the elongate body.

In Example 4, the subject matter of Example 3 is optionally configured such that the at least one second electrode is disposed on the second portion of the elongate body.

In Example 5, the subject matter of Example 4 is optionally configured such that an electrode distance between the at least one first electrode and the at least one second electrode is adjustable with movement of the second portion of the elongate body with respect to the first portion of the elongate body.

In Example 6, the subject matter of any one of Examples 1-5 optionally includes at least one second fixation structure disposed on the elongate body distally from the at least one first fixation structure.

In Example 7, the subject matter of Example 6 is optionally configured such that the at least one second fixation structure is located on the elongate body proximate the at least one first electrode.

In Example 8, the subject matter of any one of Examples 1-7 is optionally configured such that the first distance is 5-10 cm.

In Example 9, the subject matter of any one of Examples 1-8 optionally includes a sheath removably disposed around at least the at least one first fixation structure, wherein the at least one first fixation structure includes a delivery configuration with the sheath disposed around the at least one first fixation structure to constrain the at least one first fixation structure. The at least one first fixation structure includes a deployed configuration with the sheath removed from around the at least one first fixation structure to allow the at least one first fixation structure to extend outwardly from the elongate body.

In Example 10, the subject matter of any one of Examples 1-9 is optionally configured such that the at least one first fixation structure includes at least one fin.

Example 11 can include, or can optionally be combined with any one of Examples 1-10 to include subject matter that can include a stimulation lead including an elongate body including a distal end and a proximal end, wherein the elongate body includes a first portion and a second portion. The second portion is coaxially disposed around the first portion. At least one first electrode is disposed on the first portion of the elongate body proximate the distal end of the elongate body. The at least one first electrode is configured to stimulate a first target nerve. At least one second electrode is disposed on the second portion of the elongate body between the at least one first electrode and the proximal end of the elongate body. The at least one second electrode is configured to stimulate a second target nerve, wherein an electrode distance between the at least one first electrode and the at least one second electrode is adjustable with movement of the second portion of the elongate body with respect to the first portion of the elongate body.

In Example 12, the subject matter of Example 12 is optionally configured such that the at least one first electrode includes a plurality of first electrodes, and the at least one second electrode includes a plurality of second electrodes.

In Example 13, the subject matter of any one of Examples 11-12 optionally includes at least one first fixation structure disposed between the at least one second electrode and the proximal end of the elongate body. The at least one first fixation structure is configured to anchor the stimulation lead proximate the sacrum, wherein the at least one first fixation structure is located on the elongate body and spaced a first distance proximally along the elongate body from the at least one first electrode.

In Example 14, the subject matter of Example 13 optionally includes at least one second fixation structure disposed on the elongate body distally from the at least one first fixation structure.

In Example 15, the subject matter of Example 14 is optionally configured such that the at least one second fixation structure is located on the elongate body proximate the at least one first electrode.

In Example 16, the subject matter of any one of Examples 13-15 optionally includes a sheath removably disposed around at least the at least one first fixation structure, wherein the at least one first fixation structure includes a delivery configuration with the sheath disposed around the at least one first fixation structure to constrain the at least one first fixation structure. The at least one first fixation structure includes a deployed configuration with the sheath removed from around the at least one first fixation structure to allow the at least one first fixation structure to extend outwardly from the elongate body.

In Example 17, the subject matter of any one of Examples 13-16 is optionally configured such that the at least one first fixation structure includes at least one fin.

Example 18 an include, or can optionally be combined with any one of Examples 1-17 to include subject matter that can include a stimulation lead including an elongate body including a distal end and a proximal end, wherein the elongate body includes a first portion and a second portion. The second portion is coaxially disposed around the first portion. At least two first electrodes are disposed on the first portion of the elongate body proximate the distal end of the elongate body. The at least two first electrodes are configured to stimulate a first target nerve. At least two second electrodes are disposed on the second portion of the elongate body between the at least two first electrodes and the proximal end of the elongate body. The at least two second electrodes are configured to stimulate a second target nerve, wherein an electrode distance between the at least two first electrodes and the at least two second electrodes is adjustable with movement of the second portion of the elongate body with respect to the first portion of the elongate body. At least one first fixation structure is disposed between the at least two second electrodes and the proximal end of the elongate body. The at least one first fixation structure is configured to anchor the stimulation lead proximate the sacrum, wherein the at least one first fixation structure is located on the elongate body and spaced a first distance proximally along the elongate body from the at least two first electrodes.

In Example 19, the subject matter of Example 18 optionally includes at least one second fixation structure disposed on the elongate body distally from the at least one first fixation structure, wherein the at least one second fixation structure is located on the elongate body proximate the at least two first electrodes.

In Example 20, the subject matter of any one of Examples 18-19 optionally includes a sheath removably disposed around at least the at least one first fixation structure, wherein the at least one first fixation structure includes a delivery configuration with the sheath disposed around the at least one first fixation structure to constrain the at least one first fixation structure. The at least one first fixation structure includes a deployed configuration with the sheath removed from around the at least one first fixation structure to allow the at least one first fixation structure to extend outwardly from the elongate body.

DETAILED DESCRIPTION

This patent document pertains generally to apparatuses, systems, and methods for body tissue electrical stimulation and more particularly, but not by way of limitation, to apparatuses, systems, and methods for nerve electrical stimulation, including, but not limited to, sacral nerve electrical stimulation, pudendal nerve electrical stimulation, pelvic nerve electrical stimulation, peripheral nerve electrical stimulation, spinal cord electrical stimulation, vagal nerve electrical stimulation, gastric nerve electrical stimulation, and brain nerve electrical stimulation.

The present inventors have recognized, among other things, that it is desirable to provide an apparatus, system, and method to stimulate one or more nerves or other tissue. The present inventors have further recognized, among other things, that the subject matter can be used with an implantable stimulation system. The inventors have recognized that, in some examples, the pudendal nerve can be accessed via the sacral nerve and that a single stimulation device can be used to stimulate one or both of the pudendal and the sacral nerves. While primarily described with respect to stimulation leads and devices, this is merely for the sake of convenience. It should be understood that the subject matter described herein can be used with other implantable medical devices, such as needles, catheters, conductors, tubes, conduits, or the like, for instance, as well as external devices in some examples. Also, although primarily described herein as being used to stimulate a pudendal nerve and a sacral nerve, it should be understood that the stimulation leads can be used to stimulate various nerves and/or tissues and is not limited to stimulating only the pudendal nerve and the sacral nerve.

Figure 1:
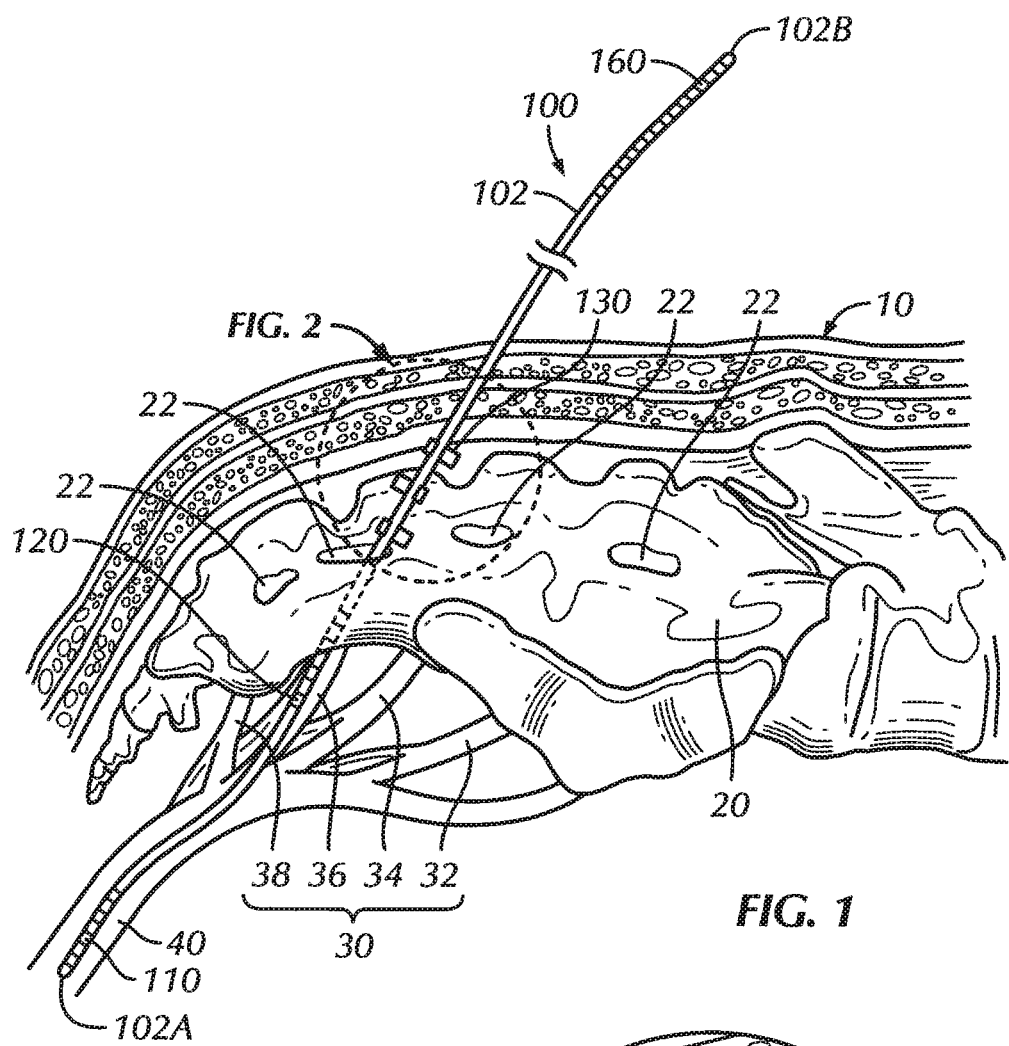
FIG. 1 shows a stimulation lead in accordance with at least one example of the invention, the stimulation lead being shown partially implanted within a patient.

Referring to FIG. 1, a stimulation lead 100 in accordance with some examples is shown partially implanted within a patient 10. A sacrum 20 of the patient 10 includes foramen 22. Sacral nerves 30 and a pudendal nerve 40 are portrayed below the sacrum 20. The sacral nerves 30 include sacral nerve S1 32, sacral nerve S2 34, sacral nerve S3 36, and sacral nerve S4 38 (herein referred to as S1, S2, S3, and S4 nerves).

Referring still to FIG. 1, using the transforaminal approach to the pudendal nerve 40, in some examples, a physician can "float" or otherwise maneuver the stimulation lead 100 along one of the S2, S3, and S4 nerves 34, 36, 38, for instance, and then continue farther to the nexus where the S2, S3, S4 nerves 34, 36, 38 come together. In some examples, the S2 nerve 34 may provide a desirable route to the pudendal nerve 40. In further examples, the S3 nerve 36 may provide a desirable route to the pudendal nerve 40 (as shown in FIG. 1). In still further examples, the S4 nerve 38 may provide a desirable route to the pudendal nerve 40.

In some examples, stimulation of the S3 nerve 36 can be beneficial for various treatments, such as, but not limited to urge incontinence, urinary frequency urgency, nonobstructive urinary retention, sexual dysfunction, fecal incontinence, constipation, and interstitial cystitis. In some examples, stimulation of the S2 nerve 34 at this level is sometimes discouraged because such stimulation can sometimes result in too much motor activity in the lower extremity. Therefore, in some examples, where the pudendal nerve 40 is accessed via the S3 nerve 36, one stimulation lead 100 can be used with spaced apart electrodes 110, 120. That is, in some examples, one set of proximal electrodes 120 to stimulate the S3 nerve 36 and one set of distal electrodes 110 to stimulate the pudendal nerve 40. However, in other examples, where the pudendal nerve 40 is accessed via the S2 nerve 34, if it is not desired to stimulate the S2 nerve 34, one lead can be used with distal electrodes to stimulate the pudendal nerve 40 and another lead can be used to be implanted proximate the S3 nerve 36 to stimulate the S3 nerve 36.

Referring again to FIG. 1, the stimulation lead 100, in some examples, includes an elongate body 102 including a distal end 102A and a proximal end 102B. In some examples, at least one first electrode 110 is disposed proximate the distal end 102A of the elongate body 102. In some examples, the stimulation lead 100 includes more than one first electrode 110, the first electrodes 110 being spaced apart by a spacing distance. In some examples, the stimulation lead 100 can include a spacing distance between the first electrodes 110 of about 1-3 mm. In some examples, the first electrodes 110 can be about 1-3 mm in length. In some examples, the stimulation lead 100 includes an array of first electrodes 110 proximate the distal end 102A of the elongate body 102. In some examples, the stimulation lead 100 includes a plurality of first electrodes 110. In some examples, the stimulation lead 100 includes four first electrodes 110, as shown in the example of FIG. 1. In some examples, the at least one first electrode 110 is configured to stimulate a first target nerve 40, such as, but not limited to the pudendal nerve 40.

In some examples, at least one second electrode 120 is disposed between the at least one first electrode 110 and the proximal end 102B of the elongate body 102. In some examples, the stimulation lead 100 includes more than one second electrode 120, the second electrodes 120 being spaced apart by a spacing distance. In some examples, the second electrodes 120 can be about 1-3 mm in length. In some examples, the stimulation lead 100 can include a spacing distance between the second electrodes 120 of about 1-3 mm. In some examples, the stimulation lead 100 includes an array of second electrodes 120 disposed between the at least one first electrode 110 and the proximal end 102B of the elongate body 102. In some examples, the stimulation lead 100 includes a plurality of second electrodes 120. In some examples, the stimulation lead 100 includes four second electrodes 120, as shown in the example of FIG. 1. In some examples, the at least one second electrode 120 is configured to stimulate a second target nerve 30, such as, but not limited to the sacral nerve 30.

In some examples, the stimulation lead 100 includes one to twelve electrodes 110, 120 in various configurations. For instance, in some examples, the stimulation lead 100 includes four first electrodes 110 located toward the distal end 102A of the stimulation lead 100 for stimulation of the pudendal nerve 40, for instance, and four second electrodes 120 spaced proximally from the first electrodes 110 for stimulation of the sacral nerve 30, for instance. In other examples, the stimulation lead 100 includes eight first electrodes 110 located toward the distal end 102A of the stimulation lead 100 for stimulation of the pudendal nerve 40, for instance, and four second electrodes 120 spaced proximally from the first electrodes 110 for stimulation of the sacral nerve 30, for instance. In some examples, the stimulation lead 100 can include six first electrodes 110 and six second electrodes 120. It should be understood that the examples described herein are merely exemplary and that other configurations of electrodes 110, 120 are contemplated herein. In various examples, any electrode configuration can be used, depending upon the nerve(s) or tissue(s) to be stimulated and the approach to be used to get to the nerve(s) and/or tissue(s). In some examples, programming (for instance, within a pulse generator) can be used to exclude electrodes 110, 120 that do not properly or sufficiently stimulate the target nerve(s) or tissue(s). For instance, an electrode can be excluded if the stimulation from the electrode has too much leg recruitment, pain, or another adverse effect.

Figure 2:
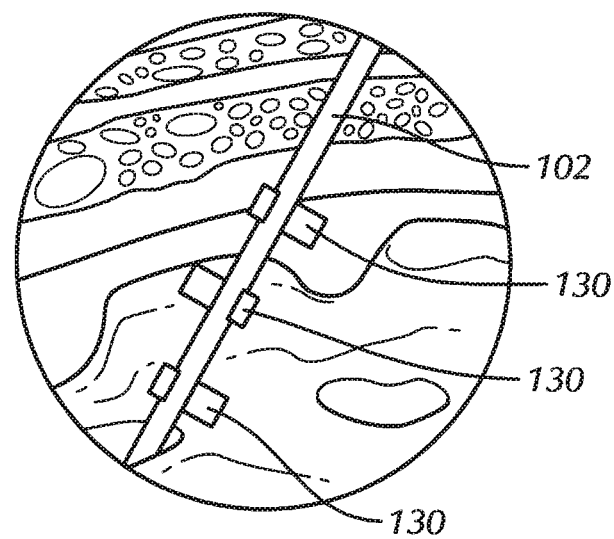
FIG. 2 is an enlarged fragmentary view of the stimulation lead of FIG. 1.

Referring now to FIGS. 1 and 2, in some examples, at least one first fixation structure 130 is disposed on the elongate body 102 for at least aiding in anchoring the stimulation lead 100 in place within the patient 10. In some examples, the at least one fixation structure 130 is disposed on the elongate body 102 between the at least one second electrode 120 and the proximal end 102B of the elongate body 102. In some examples, the at least one first fixation structure 130 is configured to anchor the stimulation lead 100 proximate the sacrum 20. In some examples, the at least one first fixation structure 130 is located on the elongate body 102 and spaced a first distance proximally along the elongate body 102 from the at least one first electrode 110. In some examples, the first distance is configured to allow the at least one first electrode 110 to be positioned proximate the first target nerve 40 with the at least one first fixation structure 130 positioned proximate the sacrum 20. In some examples, the first distance is within the range of 5-10 cm. In some examples, more than one first fixation structure 130 is contemplated. For instance, in the example shown in FIGS. 1 and 2, the elongate body 102 includes three sets of three first fixation structures 130. In some examples, the at least one first fixation structure 130 includes a fin. In other examples, the at least one first fixation structure 130 includes other fixation structures, such as tines, barbs, coils, or the like. It is noted that, in various examples, different numbers, sizes, and/or types of fixation structures can be used with the stimulation lead 100, for instance to adjust or tune fixation of the stimulation lead 100 within the patient 10. In some examples, the at least one first fixation structure 130 provides main anchoring (major fixation) of the stimulation lead 100.

Referring again to FIG. 1, the stimulation lead 100, in some examples, includes one or more contacts 160 proximate the proximal end 102B of the elongate body 102. The one or more contacts 160, in some examples, are equal in number to the total number of electrodes 110, 120 on the stimulation lead 100. In some examples, the stimulation lead 100 includes conductors running between the one or more contacts 160 and the corresponding one or more electrodes 110, 120. In the example shown in FIG. 1, the stimulation lead 100 includes eight contacts 160, corresponding to the four first electrodes 110 and the four second electrodes 120. In other examples, various other numbers and/or configurations of connectors 160 are contemplated, depending upon various factors, such as, but not limited to, the number of electrodes on the stimulation lead, the device to which the stimulation lead is to be connected, or the like. The one or more contacts 160, in some examples, are configured for electrically coupling to one or more connectors, for instance, within a pulse generator or other medical device or a lead extension to which the stimulation lead 100 is intended to be connected. In some examples, the one or more contacts 160 are configured to electrically couple the one or more electrodes 110, 120 to the pulse generator to transmit electrical stimulation pulses generated by the pulse generator to the appropriate one or more electrodes 110, 120 and, in turn, to the appropriate target nerves 30, 40 and/or target tissue.

Figure 3:
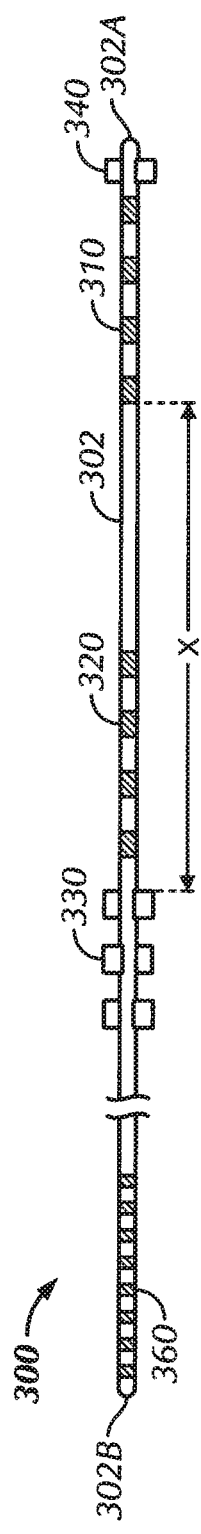
FIG. 3 shows a stimulation lead in accordance with at least one example of the invention.

Referring now to FIG. 3, a stimulation lead 300 in accordance with some examples is shown for at least partial implantation within a patient. The stimulation lead 300, in some examples, is substantially similar to the stimulation lead 100 described herein and/or can be used in substantially similar ways to those described herein with respect to the stimulation lead 100. The stimulation lead 300, in some examples, includes an elongate body 302 including a distal end 302A and a proximal end 302B.

In some examples, at least one first electrode 310 is disposed proximate the distal end 302A of the elongate body 302. In some examples, the stimulation lead 300 includes more than one first electrode 310, the first electrodes 310 being spaced apart by a spacing distance. In some examples, the stimulation lead 300 can include a spacing distance between the first electrodes 310 of about 1-3 mm. In some examples, the first electrodes 310 can be about 1-3 mm in length. In some examples, the stimulation lead 300 includes an array of first electrodes 310 proximate the distal end 302A of the elongate body 302. In some examples, the stimulation lead 300 includes a plurality of first electrodes 310. In some examples, the stimulation lead 300 includes four first electrodes 310, as shown in the example of FIG. 3. In some examples, the at least one first electrode 310 is configured to stimulate a first target nerve, such as, but not limited to the pudendal nerve.

In some examples, at least one second electrode 320 is disposed between the at least one first electrode 310 and the proximal end 302B of the elongate body 302. In some examples, the stimulation lead 300 includes more than one second electrode 320, the second electrodes 320 being spaced apart by a spacing distance. In some examples, the second electrodes 320 can be about 1-3 mm in length. In some examples, the stimulation lead 300 can include a spacing distance between the second electrodes 320 of about 1-3 mm. In some examples, the stimulation lead 300 includes an array of second electrodes 320 disposed between the at least one first electrode 310 and the proximal end 302B of the elongate body 302. In some examples, the stimulation lead 300 includes a plurality of second electrodes 320. In some examples, the stimulation lead 300 includes four second electrodes 320, as shown in the example of FIG. 3. In some examples, the at least one second electrode 320 is configured to stimulate a second target nerve, such as, but not limited to the sacral nerve.

In some examples, the stimulation lead 300 includes one to twelve electrodes 310, 320 in various configurations. For instance, in some examples, the stimulation lead 300 includes four first electrodes 310 located toward the distal end 302A of the stimulation lead 300 for stimulation of the pudendal nerve, for instance, and four second electrodes 320 spaced proximally from the first electrodes 310 for stimulation of the sacral nerve, for instance. In other examples, the stimulation lead 300 includes eight first electrodes 310 located toward the distal end 302A of the stimulation lead 300 for stimulation of the pudendal nerve, for instance, and four second electrodes 320 spaced proximally from the first electrodes 310 for stimulation of the sacral nerve, for instance. In some examples, the stimulation lead 300 can include six first electrodes 310 and six second electrodes 320. It should be understood that the examples described herein are merely exemplary and that other configurations of electrodes 310, 320 are contemplated herein. In various examples, any electrode configuration can be used, depending upon the nerve(s) or tissue(s) to be stimulated and the approach to be used to get to the nerve(s) and/or tissue(s). In some examples, programming (for instance, within a pulse generator) can be used to exclude electrodes 310, 320 that do not properly or sufficiently stimulate the target nerve(s) or tissue(s). For instance, an electrode can be excluded if the stimulation from the electrode has too much leg recruitment, pain, or another adverse effect.

In some examples, at least one first fixation structure 330 is disposed on the elongate body 302 for at least aiding in anchoring the stimulation lead 300 in place within the patient. In some examples, the at least one fixation structure 330 is disposed on the elongate body 302 between the at least one second electrode 320 and the proximal end 302B of the elongate body 302. In some examples, the at least one first fixation structure 330 is configured to anchor the stimulation lead 300 proximate the sacrum. In some examples, the at least one first fixation structure 330 is located on the elongate body 302 and spaced a first distance X proximally along the elongate body 302 from the at least one first electrode 310. In some examples, the first distance X is configured to allow the at least one first electrode 310 to be positioned proximate the first target nerve with the at least one first fixation structure 330 positioned proximate the sacrum. In some examples, the first distance X is within the range of 5-10 cm. In some examples, more than one first fixation structure 330 is contemplated. For instance, in the example shown in FIG. 3, the elongate body 302 includes three sets of three first fixation structures 330. In some examples, the at least one first fixation structure 330 includes a fin. In other examples, the at least one first fixation structure 330 includes other fixation structures, such as tines, barbs, coils, or the like. It is noted that, in various examples, different numbers, sizes, and/or types of fixation structures can be used with the stimulation lead 300, for instance to adjust or tune fixation of the stimulation lead 300 within the patient. In some examples, the at least one first fixation structure 330 provides main anchoring (major fixation) of the stimulation lead 300.

In some examples, the stimulation lead 300 includes at least one second fixation structure 340 disposed on the elongate body 302 distally from the at least one first fixation structure 330. In some examples, the at least one second fixation structure 340 is located on the elongate body 302 proximate the at least one first electrode 310. In some examples, the at least one second fixation structure 340 is located on the elongate body 302 proximate the distal end 302A of the elongate body 302. In the example shown in FIG. 3, the elongate body 302 includes one set of three second fixation structures 340. In other examples, other numbers and/or configurations of second fixation structures are contemplated. The at least one second fixation structure 340 is configured to at least partially anchor the stimulation lead 300 in place within the patient. For instance, in some examples, the at least one second fixation structure 340 at least partially anchors the distal end 302A of the elongate body 302 within the patient, such as, but not limited to, at a location proximate the pudendal nerve. In some examples, the at least one second fixation structure 340 includes a fin. In other examples, the at least one second fixation structure 340 includes other fixation structures, such as tines, barbs, coils, or the like. It is noted that, in various examples, different numbers, sizes, and/or types of fixation structures can be used with the stimulation lead 300, for instance to adjust or tune fixation of the stimulation lead 300 within the patient. In some examples, the at least one second fixation structure 340 is configured to hold the stimulation lead 300 in place with respect to the first target nerve, such as, for instance, the pudendal nerve. In some examples, the at least one second fixation structure 340 is less rigid than the at least one first fixation structure 330. In some examples, the at least one second fixation structure 340 can be deployable, for instance, once the at least one second fixation structure 340 is past the first and/or second target nerve to inhibit nerve damage during implantation.

The stimulation lead 300, in some examples, includes one or more contacts 360 proximate the proximal end 302B of the elongate body 302. The one or more contacts 360, in some examples, are equal in number to the total number of electrodes 310, 320 on the stimulation lead 300. In some examples, the stimulation lead 300 includes conductors running between the one or more contacts 360 and the corresponding one or more electrodes 310, 320. In the example shown in FIG. 3, the stimulation lead 300 includes eight contacts 360, corresponding to the four first electrodes 310 and the four second electrodes 320. In other examples, various other numbers and/or configurations of connectors 360 are contemplated, depending upon various factors, such as, but not limited to, the number of electrodes on the stimulation lead, the device to which the stimulation lead is to be connected, or the like. The one or more contacts 360, in some examples, are configured for electrically coupling to one or more connectors, for instance, within a pulse generator or other medical device or a lead extension to which the stimulation lead 300 is intended to be connected. In some examples, the one or more contacts 360 are configured to electrically couple the one or more electrodes 310, 320 to the pulse generator to transmit electrical stimulation pulses generated by the pulse generator to the appropriate one or more electrodes 310, 320 and, in turn, to the appropriate target nerves and/or target tissue.

Figure 4:
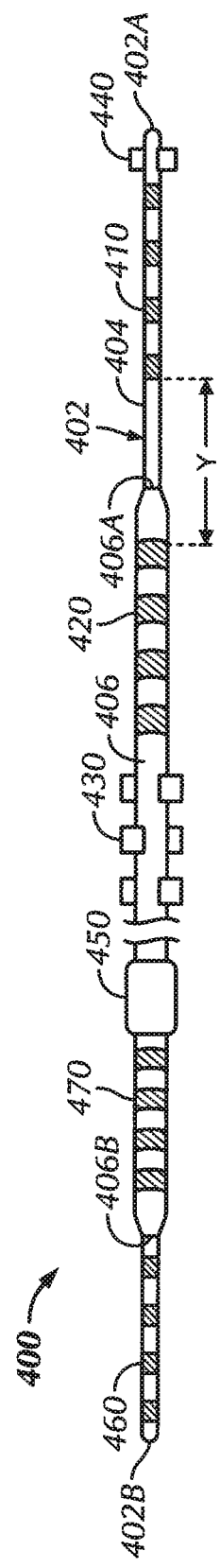
FIG. 4 shows a stimulation lead in accordance with at least one example of the invention.

Referring now to FIG. 4, a stimulation lead 400 in accordance with some examples is shown for at least partial implantation within a patient. The stimulation lead 400, in some examples, is substantially similar to the stimulation lead 100, 300 described herein and/or can be used in substantially similar ways to those described herein with respect to the stimulation lead 100, 300. The stimulation lead 400, in some examples, includes an elongate body 402 including a distal end 402A and a proximal end 402B. In some examples, the elongate body 402 includes a first portion 404 and a second portion 406, with the second portion 406 being coaxially disposed around the first portion 404. In some examples, with the stimulation lead 400 in place within the patient, the first portion 404 extends distally from a distal end 406A of the second portion 406. In some examples, the first and second portions 404, 406 are coaxial with the first portion 404 being at least partially disposed within the second portion 406. In some examples, such a coaxial lead configuration of the stimulation lead 400 allows the physician or other caregiver to find one nerve (for instance, the sacral nerve) with the second portion 406, and then run the first portion 404 through the second portion 406 to find another nerve (for instance, the pudendal nerve).

In some examples, at least one first electrode 410 is disposed proximate the distal end 402A of the elongate body 402. In some examples, the at least one first electrode 410 is disposed on the first portion 404 of the elongate body 402. In some examples, the stimulation lead 400 includes more than one first electrode 410, the first electrodes 410 being spaced apart by a spacing distance. In some examples, the stimulation lead 400 can include a spacing distance between the first electrodes 410 of about 1-3 mm. In some examples, the first electrodes 410 can be about 1-3 mm in length. In some examples, the stimulation lead 400 includes an array of first electrodes 410 proximate the distal end 402A of the elongate body 402. In some examples, the stimulation lead 400 includes a plurality of first electrodes 410. In some examples, the stimulation lead 400 includes four first electrodes 410, as shown in the example of FIG. 4. In some examples, the at least one first electrode 410 is configured to stimulate a first target nerve, such as, but not limited to the pudendal nerve.

In some examples, at least one second electrode 420 is disposed between the at least one first electrode 410 and the proximal end 402B of the elongate body 402. In some examples, the at least one second electrode 420 is disposed on the second portion 406 of the elongate body 402. In some examples, with the at least one first electrode 410 disposed on the first portion 404 and the at least second electrode 420 disposed on the second portion 406, an electrode distance Y between the at least one first electrode 410 and the at least one second electrode 420 is adjustable with movement of the second portion 406 of the elongate body 402 with respect to the first portion 404 of the elongate body 402.

In some examples, the stimulation lead 400 includes more than one second electrode 420, the second electrodes 420 being spaced apart by a spacing distance. In some examples, the second electrodes 420 can be about 1-3 mm in length. In some examples, the stimulation lead 400 can include a spacing distance between the second electrodes 420 of about 1-3 mm. In some examples, the stimulation lead 400 includes an array of second electrodes 420 disposed between the at least one first electrode 410 and the proximal end 402B of the elongate body 402. In some examples, the stimulation lead 400 includes a plurality of second electrodes 420. In some examples, the stimulation lead 400 includes four second electrodes 420, as shown in the example of FIG. 4. In some examples, the at least one second electrode 420 is configured to stimulate a second target nerve, such as, but not limited to the sacral nerve.

In some examples, the stimulation lead 400 includes one to twelve electrodes 410, 420 in various configurations. For instance, in some examples, the stimulation lead 400 includes four first electrodes 410 located toward the distal end 402A of the stimulation lead 400 for stimulation of the pudendal nerve, for instance, and four second electrodes 420 spaced proximally from the first electrodes 410 for stimulation of the sacral nerve, for instance. In other examples, the stimulation lead 400 includes eight first electrodes 410 located toward the distal end 402A of the stimulation lead 400 for stimulation of the pudendal nerve, for instance, and four second electrodes 420 spaced proximally from the first electrodes 410 for stimulation of the sacral nerve, for instance. In some examples, the stimulation lead 400 can include six first electrodes 410 and six second electrodes 420. It should be understood that the examples described herein are merely exemplary and that other configurations of electrodes 410, 420 are contemplated herein. In various examples, any electrode configuration can be used, depending upon the nerve(s) or tissue(s) to be stimulated and the approach to be used to get to the nerve(s) and/or tissue(s). In some examples, programming (for instance, within a pulse generator) can be used to exclude electrodes 410, 420 that do not properly or sufficiently stimulate the target nerve(s) or tissue(s). For instance, an electrode can be excluded if the stimulation from the electrode has too much leg recruitment, pain, or another adverse effect.

Moreover, with the first portion 404 and the second portion 406 of the elongate body 402 being movable with respect to one another and the electrode distance Y being variable, a physician or other caregiver implanting the stimulation lead 400 is more flexible with where he places the at least one first electrode 410 with respect to the first target nerve or tissue and where he places the at least one second electrode 420 with respect to the second target nerve or tissue. That is, the physician or other caregiver is not confined to a given electrode distance between first and second electrodes, such as, for instance, on a single elongate body. Instead, the physician or other caregiver, in some examples, can place the at least one first electrode 410 in a desired location with respect to the first target nerve or tissue and the at least one second electrode 420 in a desired location with respect to the second target nerve or tissue. In some examples, once the second portion 406 of the elongate body 402 is in place with respect to the first portion 404 of the elongate body 402, the first portion 404 and the second portion 406 can be fixed with respect to one another. In some examples, an attachment device 450 can be used to fix the first portion 404 with respect to the second portion 406. In some examples, the attachment device 450 can include a suture sleeve or anchor that, with tightening of a suture, compresses the second portion 406 against the first portion 404, thereby compressively engaging the first portion 404 with respect to the second portion 406. In other examples, the attachment device 450 can include a crimp sleeve that, with squeezing of the crimp sleeve, compresses the second portion 406 against the first portion 404, thereby compressively engaging the first portion 404 with respect to the second portion 406. In still other examples, the first portion 404 can be threadedly engaged with the second portion 406 for threaded advancement of the first portion 404 with respect to the second portion 406. It is noted that the example attachment devices 450 described above are just but a few of the possible attachment devices 450 and that, in various examples, different attachment devices 450 can be used with the stimulation lead 400 to fix the first portion 404 with respect to the second portion 406.

In some examples, the first portion 404 can include no electrodes or can include electrodes that are excluded if the stimulation lead 400 is intended only for stimulation of the first target nerve, such as, for instance, the pudendal nerve.

For instance, in some examples, if approaching the pudendal nerve along the S2 nerve, the first portion 404 can be used to follow along the S2 nerve and establish the trajectory of the stimulation lead 400 in order to pass the second portion 406 through the first portion 404 to then follow down to the pudendal nerve. Since stimulation of the S2 nerve, in some examples, is not desirable, the first portion 404 can be devoid of electrodes or the electrodes of the first portion 404 can be excluded or turned off so as not to stimulate the S2 nerve.

In some examples, at least one first fixation structure 430 is disposed on the elongate body 402 for at least aiding in anchoring the stimulation lead 400 in place within the patient. In some examples, the at least one fixation structure 430 is disposed on the elongate body 402 between the at least one second electrode 420 and the proximal end 402B of the elongate body 402. In some examples, the at least one first fixation structure 430 is configured to anchor the stimulation lead 400 proximate the sacrum. In some examples, the at least one first fixation structure 430 is disposed on the second portion 406 of the elongate body 402. In some examples, with the at least one first fixation structure 430 located on the second portion 406 of the elongate body 402, a first distance measured proximally along the elongate body 402 from the at least one first electrode 410, like the electrode distance Y, is variable and selectively adjustable by the physician or other caregiver. In some examples, the first distance can be set (by adjusting the first portion 404 with respect to the second portion 406) to allow the at least one first electrode 410 to be positioned proximate the first target nerve with the at least one first fixation structure 430 positioned proximate the sacrum. In some examples, the first distance can be set to within the range of 5-10 cm. In some examples, more than one first fixation structure 430 is contemplated. For instance, in the example shown in FIG. 4, the elongate body 402 includes three sets of three first fixation structures 430. In some examples, the at least one first fixation structure 430 includes a fin. In other examples, the at least one first fixation structure 430 includes other fixation structures, such as tines, barbs, coils, or the like. It is noted that, in various examples, different numbers, sizes, and/or types of fixation structures can be used with the stimulation lead 400, for instance to adjust or tune fixation of the stimulation lead 400 within the patient. In some examples, the at least one first fixation structure 430 provides main anchoring (major fixation) of the stimulation lead 400.

In some examples, the stimulation lead 400 includes at least one second fixation structure 440 disposed on the elongate body 402 distally from the at least one first fixation structure 430. In some examples, the at least one second fixation structure 440 is located on the elongate body 402 proximate the at least one first electrode 410. In some examples, the at least one second fixation structure 440 is located on the elongate body 402 proximate the distal end 402A of the elongate body 402. In some examples, the at least one second fixation structure 440 is located on the first portion 404 of the elongate body 402. In the example shown in FIG. 4, the elongate body 402 includes one set of three second fixation structures 440. In other examples, other numbers and/or configurations of second fixation structures are contemplated. The at least one second fixation structure 440 is configured to at least partially anchor the stimulation lead 400 in place within the patient. For instance, in some examples, the at least one second fixation structure 440 at least partially anchors the distal end 402A of the elongate body 402 within the patient, such as, but not limited to, at a location proximate the pudendal nerve. In some examples, the at least one second fixation structure 440 includes a fin. In other examples, the at least one second fixation structure 340 includes other fixation structures, such as tines, barbs, coils, or the like. It is noted that, in various examples, different numbers, sizes, and/or types of fixation structures can be used with the stimulation lead 400, for instance to adjust or tune fixation of the stimulation lead 400 within the patient. In other examples, the stimulation lead 400 includes no second fixation structures. In some examples, the at least one second fixation structure 440 is configured to hold the stimulation lead 400 in place with respect to the first target nerve, such as, for instance, the pudendal nerve. In some examples, the at least one second fixation structure 440 is less rigid than the at least one first fixation structure 430. In some examples, the at least one second fixation structure 440 can be deployable, for instance, once the at least one second fixation structure 440 is past the first and/or second target nerve to inhibit nerve damage during implantation.

The stimulation lead 400, in some examples, includes one or more first contacts 460 proximate the proximal end 402B of the elongate body 402. In some examples, the one or more first contacts 460 are disposed on a proximal portion of the first portion 404 of the elongate body 402 with the first portion 404 extending proximally from a proximal end 406B of the second portion 406. In some examples, the stimulation lead 400 includes one or more second contacts 470 proximate the proximal end 402B of the elongate body 402. In some examples, the one or more second contacts 470 are disposed on the second portion 406 of the elongate body 402 proximate the proximal end 406B of the second portion 406. The one or more first and second contacts 460, 470, in some examples, are equal in number to the total number of electrodes 410, 320 on the stimulation lead 400. In some examples, the stimulation lead 400 includes conductors running between the one or more first contacts 460 and the corresponding one or more first electrodes 410 and running between the one or more second contacts 470 and the corresponding one or more second electrodes 420. In the example shown in FIG. 4, the stimulation lead 400 includes four first contacts 460 and four second contacts 470, corresponding to the four first electrodes 410 and the four second electrodes 420, respectively. In other examples, various other numbers and/or configurations of first and second connectors 460, 470 are contemplated, depending upon various factors, such as, but not limited to, the number of electrodes on the stimulation lead, the device to which the stimulation lead is to be connected, or the like. The one or more first and second contacts 460, 470, in some examples, are configured for electrically coupling to one or more connectors, for instance, within a pulse generator or other medical device or a lead extension to which the stimulation lead 400 is intended to be connected. In some examples, the one or more first and second contacts 460, 470 are configured to electrically couple the one or more electrodes 410, 420 to the pulse generator to transmit electrical stimulation pulses generated by the pulse generator to the appropriate one or more electrodes 410, 420 and, in turn, to the appropriate target nerves and/or target tissue.

Figure 5A:
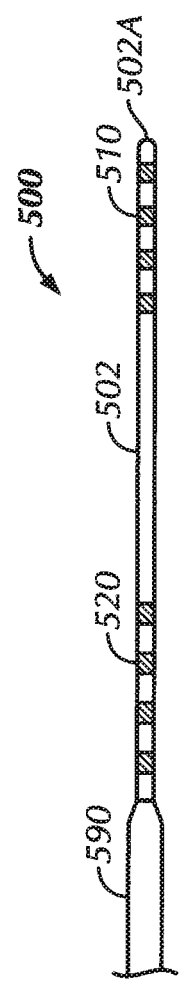
FIG. 5A shows a stimulation lead in accordance with at least one example of the invention, the stimulation lead including a sheath disposed over first fixation structures.
Figure 5B:
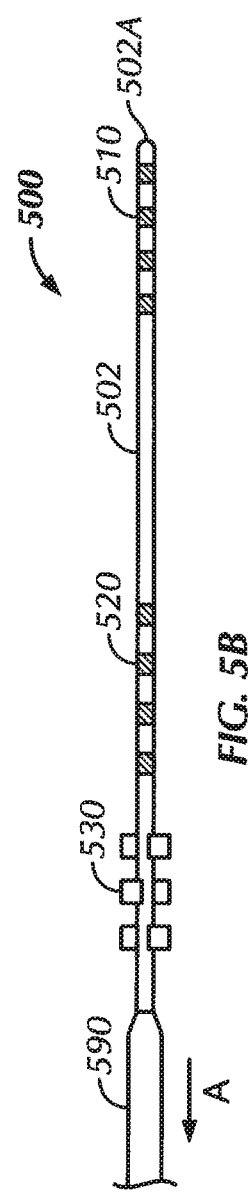
FIG. 5B shows the stimulation lead of FIG. 5A with the sheath retracted to uncover the first fixation structures.

Referring now to FIG. 5, a stimulation lead 500 in accordance with some examples is shown for at least partial implantation within a patient. The stimulation lead 500, in some examples, is substantially similar to the stimulation lead 100, 300, 400 described herein and/or can be used in substantially similar ways to those described herein with respect to the stimulation lead 100, 300, 400. The stimulation lead 500, in some examples, includes an elongate body 502 including a distal end 502A and a proximal end.

In some examples, at least one first electrode 510 is disposed proximate the distal end 502A of the elongate body 502. In some examples, the stimulation lead 500 includes more than one first electrode 510, the first electrodes 510 being spaced apart by a spacing distance. In some examples, the stimulation lead 500 can include a spacing distance between the first electrodes 510 of about 1-3 mm. In some examples, the first electrodes 510 can be about 1-3 mm in length. In some examples, the stimulation lead 500 includes an array of first electrodes 510 proximate the distal end 502A of the elongate body 502. In some examples, the stimulation lead 500 includes a plurality of first electrodes 510. In some examples, the stimulation lead 500 includes four first electrodes 510, as shown in the example of FIG. 5. In some examples, the at least one first electrode 510 is configured to stimulate a first target nerve, such as, but not limited to the pudendal nerve. In various examples, any electrode configuration can be used, depending upon the nerve(s) or tissue(s) to be stimulated and the approach to be used to get to the nerve(s) and/or tissue(s).

In some examples, at least one second electrode 520 is disposed between the at least one first electrode 510 and the proximal end 502B of the elongate body 502. In some examples, the stimulation lead 500 includes more than one second electrode 520, the second electrodes 520 being spaced apart by a spacing distance. In some examples, the second electrodes 520 can be about 1-3 mm in length. In some examples, the stimulation lead 500 can include a spacing distance between the second electrodes 520 of about 1-3 mm. In some examples, the stimulation lead 500 includes an array of second electrodes 520 disposed between the at least one first electrode 510 and the proximal end 502B of the elongate body 502. In some examples, the stimulation lead 500 includes a plurality of second electrodes 520. In some examples, the stimulation lead 500 includes four second electrodes 520, as shown in the example of FIG. 5. In some examples, the at least one second electrode 520 is configured to stimulate a second target nerve, such as, but not limited to, the sacral nerve. In various examples, any electrode configuration can be used, depending upon the nerve(s) or tissue(s) to be stimulated and the approach to be used to get to the nerve(s) and/or tissue(s).

In some examples, at least one first fixation structure 530 is disposed on the elongate body 502 for at least aiding in anchoring the stimulation lead 500 in place within the patient. In some examples, the at least one fixation structure 530 is disposed on the elongate body 502 between the at least one second electrode 520 and the proximal end of the elongate body 502. In some examples, the at least one first fixation structure 530 is configured to anchor the stimulation lead 500 proximate the sacrum. In some examples, the at least one first fixation structure 530 is located on the elongate body 502 and spaced a first distance proximally along the elongate body 502 from the at least one first electrode 510. In some examples, the first distance is configured to allow the at least one first electrode 510 to be positioned proximate the first target nerve with the at least one first fixation structure 530 positioned proximate the sacrum. In some examples, the first distance is within the range of 5-10 cm. In some examples, more than one first fixation structure 530 is contemplated. For instance, in the example shown in FIG. 5, the elongate body 502 includes three sets of three first fixation structures 530. In some examples, the at least one first fixation structure 530 includes a fin. In other examples, the at least one first fixation structure 530 includes other fixation structures, such as tines, barbs, coils, or the like. It is noted that, in various examples, different numbers, sizes, and/or types of fixation structures can be used with the stimulation lead 500, for instance to adjust or tune fixation of the stimulation lead 500 within the patient. In some examples, the at least one first fixation structure 530 provides main anchoring (major fixation) of the stimulation lead 500.

In some examples, the at least one first fixation structure 530 of the stimulation lead 500 includes one or more deployable fixation structures 530 to allow the physician or other caregiver to make sure the stimulation lead 500 is in the proper location before deploying the one or more deployable fixation structures 530. For instance, in some examples, such a configuration allows the physician or other caregiver to make sure that the chosen sacral nerve (S2, S3, or S4 nerve, for instance) is the correct access for the pudendal nerve before deploying the at least one first fixation structure 530.

In some examples, a sheath 590 is removably disposed around at least the at least one first fixation structure 530 for selectively deploying the at least one first fixation structure 530. In such examples, the at least one first fixation structure 530 includes a delivery configuration with the sheath 590 disposed around the at least one first fixation structure 530 to constrain the at least one first fixation structure 530 against the elongate body 502 and/or inhibit the at least one first fixation structure 530 from engaging tissue of the patient and at least partially anchoring the stimulation lead 500 in place within the patient. Further, in such examples, the at least one first fixation structure 530 includes a deployed configuration with the sheath 590 removed from around the at least one first fixation structure 530 to allow the at least one first fixation structure 530 to extend outwardly from the elongate body 502. In some examples, the sheath 590 is removed from around the at least one first fixation structure 530 by pulling the sheath 590 in direction A with respect to the stimulation lead 500 to uncover the at least one first fixation structure 530. The at least one first fixation structure 530, in some examples, is biased to the deployed configuration, so, with the sheath 590 pulled back and uncovering the at least one first fixation structure 530, the at least one first fixation structure 530 is free to move to the deployed configuration to contact tissue of the patient and at least partially anchor the stimulation lead 500 in place within the patient.

In some examples, a sheath, similar to that described herein with respect to the stimulation lead 500, can be similarly used with stimulation leads 100, 300, 400 described herein. For instance, referring again to FIG. 4, with respect to the stimulation lead 400, in some examples, the first portion 404 allows the physician to determine the proper trajectory of the stimulation lead 400 before deploying the at least one first fixation structure 430. In some examples, the physician or other caregiver can map as the stimulation lead 400 is implanting (for instance, using test stimulations and measuring responses to approach the target nerve). Then, when the stimulation lead 400 is in the proper position with respect to the second target nerve, such as, for instance, the sacral nerve. Once in place, the at least one first fixation structure 430 can be deployed (for instance, by removing a sheath similar to the sheath 590 from around the first portion 404), and the second portion 406 can be run through the first portion 404 to extend beyond the first portion 404 to find the first target nerve, such as, for instance, the pudendal nerve. Once the second portion 406 is in place, in some examples, the attachment device 450 can be secured, affixed, compressed, or otherwise actuated to engage the second portion 406 to the first portion 404 to inhibit the first and second portions 404, 406 from moving with respect to one another. In some examples, such as examples in which the stimulation lead 400 includes at least one second fixation structure 440, another sheath (for instance, similar to the sheath 590) can be used to cover and retain the at least one second fixation structure 440 in a delivery configuration until which point that the physician or other caregiver is ready to anchor the first portion 404. At this point, the other sheath can be removed from covering the at least one second fixation structure 440, allowing the at least one second fixation structure 440 to move to the deployed configuration to at least partially anchor the first portion 404 with respect to the patient.

The present inventors have recognized various advantages of the subject matter described herein. For instance, in some examples, the apparatuses, systems, and methods described herein can be used to stimulate one or more nerves or other tissue. The present inventors have recognized, among other things, that the subject matter can be used with an implantable stimulation system. The inventors have further recognized that, in some examples, the pudendal nerve can be accessed via the sacral nerve and that a single stimulation device can be used to stimulate one or both of the pudendal and the sacral nerves. While various advantages of the example apparatuses, systems, and methods are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A stimulation lead comprising:
   an elongate body including a distal end and a proximal end;
   at least one first electrode disposed proximate the distal end of the elongate body, the at least one first electrode configured to stimulate a first target nerve, wherein the elongate body includes a first portion and a second portion, wherein the second portion is coaxially disposed around the first portion, the at least one first electrode being disposed on the first portion of the elongate body;
   at least one second electrode disposed between the at least one first electrode and the proximal end of the elongate body, the at least one second electrode configured to stimulate a second target nerve; and
   at least one first fixation structure disposed between the at least one second electrode and the proximal end of the elongate body, the at least one first fixation structure being configured to anchor the stimulation lead proximate the sacrum, wherein the at least one first fixation structure is located on the elongate body and spaced a first distance proximally along the elongate body from the at least one first electrode.

2. The stimulation lead of claim 1, wherein the at least one first electrode includes a plurality of first electrodes, and the at least one second electrode includes a plurality of second electrodes.

3. The stimulation lead of claim 1, wherein the at least one second electrode is disposed on the second portion of the elongate body.

4. The stimulation lead of claim 3, wherein an electrode distance between the at least one first electrode and the at least one second electrode is adjustable with movement of the second portion of the elongate body with respect to the first portion of the elongate body.

5. The stimulation lead of claim 1, comprising at least one second fixation structure disposed on the elongate body distally from the at least one first fixation structure.

6. The stimulation lead of claim 5, wherein the at least one second fixation structure is located on the elongate body proximate the at least one first electrode.

7. The stimulation lead of claim 1, wherein the first distance is 5-10 cm.

8. The stimulation lead of claim 1, comprising a sheath removably disposed around at least the at least one first fixation structure, wherein the at least one first fixation structure includes:
   a delivery configuration with the sheath disposed around the at least one first fixation structure to constrain the at least one first fixation structure; and
   a deployed configuration with the sheath removed from around the at least one first fixation structure to allow the at least one first fixation structure to extend outwardly from the elongate body.

9. The stimulation lead of claim 1, wherein the at least one first fixation structure includes at least one fin.

10. A stimulation lead comprising:
    an elongate body including a first end and a second end;
    a first electrode disposed proximate the first end of the elongate body, the first electrode being configured to stimulate a first target nerve, wherein the elongate body includes a first portion and a second portion, wherein the second portion is coaxially disposed around the first portion, the first electrode being disposed on the first portion of the elongate body;
    a second electrode disposed on the second portion of the elongate body and between the first electrode and the second end of the elongate body, the second electrode being configured to stimulate a second target nerve; and
    a first fixation structure disposed between the second electrode and the second end of the elongate body, the first fixation structure being configured to anchor the stimulation lead proximate the sacrum, wherein the first fixation structure is located on the elongate body and spaced a first distance proximally along the elongate body from the first electrode.

11. The stimulation lead of claim 10, further comprising a plurality of additional first electrodes and a plurality of additional second electrodes.

12. The stimulation lead of claim 10, wherein:
    an electrode distance between the first electrode and the second electrode is adjustable with movement of the second portion of the elongate body with respect to the first portion of the elongate body.

13. The stimulation lead of claim 10, further comprising a second fixation structure disposed on the elongate body distally from the first fixation structure, wherein the second fixation structure is located on the elongate body proximate the first electrode.

14. The stimulation lead of claim 10, further comprising a sheath removably disposed around the first fixation structure, wherein the first fixation structure includes:
    a delivery configuration with the sheath disposed around the first fixation structure to constrain the first fixation structure; and
    a deployed configuration with the sheath removed from around the first fixation structure to allow the first fixation structure to extend outwardly from the elongate body.

15. The stimulation lead of claim 10, wherein the first fixation structure includes a fin.

16. A stimulation lead comprising:
    an elongate body including a first end and a second end, wherein the elongate body includes a first portion and a second portion, the second portion being coaxially disposed around the first portion;
    a first electrode disposed on the first portion of the elongate body and proximate the first end of the elongate body, the first electrode being configured to stimulate a first target nerve;
    a second electrode disposed on the second portion of the elongate body and between the first electrode and the second end of the elongate body, the second electrode being configured to stimulate a second target nerve, wherein an electrode distance between the first electrode and the second electrode is adjustable with movement of the second portion of the elongate body with respect to the first portion of the elongate body;

a first fixation structure disposed between the second electrode and the second end of the elongate body, the first fixation structure including a fin and being configured to anchor the stimulation lead proximate the sacrum, wherein the first fixation structure is located on the elongate body and spaced a first distance proximally along the elongate body from the first electrode; and a second fixation structure disposed on the elongate body distally from the first fixation structure, wherein the second fixation structure is located on the elongate body proximate the first electrode.

17. The stimulation lead of claim 16, further comprising a sheath removably disposed around the first fixation structure, wherein the first fixation structure includes:

a delivery configuration with the sheath disposed around the first fixation structure to constrain the first fixation structure; and a deployed configuration with the sheath removed from around the first fixation structure to allow the first fixation structure to extend outwardly from the elongate body.

18. The stimulation lead of claim 1, wherein one of the first target nerve and the second target nerve is a sacral nerve, and another one of the first target nerve and the second target nerve is a pudendal nerve.

19. The stimulation lead of claim 10, wherein one of the first target nerve and the second target nerve is a sacral nerve, and another one of the first target nerve and the second target nerve is a pudendal nerve.

20. The stimulation lead of claim 16, wherein one of the first target nerve and the second target nerve is a sacral nerve, and another one of the first target nerve and the second target nerve is a pudendal nerve.

* * * * *